United States Patent
Duval

(10) Patent No.: US 10,682,124 B2
(45) Date of Patent: Jun. 16, 2020

(54) AUTOMATED COLLECTION AND ANALYSIS OF BODY FLUIDS

(71) Applicant: Ur24 Technology, LLC, San Clemente, CA (US)

(72) Inventor: Landon Duval, San Clemente, CA (US)

(73) Assignee: Ur24 Technology, LLC, San Clemente, CA (US)

( * ) Notice: Subject to any disclaimer, the term of this patent is extended or adjusted under 35 U.S.C. 154(b) by 210 days.

(21) Appl. No.: 15/416,272

(22) Filed: Jan. 26, 2017

(65) Prior Publication Data

US 2017/0238911 A1  Aug. 24, 2017

Related U.S. Application Data

(63) Continuation-in-part of application No. 15/412,049, filed on Jan. 22, 2017.

(Continued)

(51) Int. Cl.
*A61B 10/00* (2006.01)
*A61B 5/20* (2006.01)
(Continued)

(52) U.S. Cl.
CPC ............ *A61B 10/007* (2013.01); *A61B 5/207* (2013.01); *G01N 33/48778* (2013.01); *G01N 33/493* (2013.01)

(58) Field of Classification Search
CPC ........ A61B 10/007; A61B 5/20; A61B 5/207; A61B 5/208; G01N 33/48778; G01N 33/493

(Continued)

(56) References Cited

U.S. PATENT DOCUMENTS

| 660,388 A | 10/1900 | Moberg et al. |
| 2,483,079 A | 9/1949 | Williams |

(Continued)

FOREIGN PATENT DOCUMENTS

| DE | 19602299 | 7/1997 |
| EP | 0 951 881 | 6/2000 |

(Continued)

OTHER PUBLICATIONS

International Search Report and Written Opinion issued in PCT Application No. PCT/US2017/016626, dated Apr. 21, 2017, in 7 pages.

(Continued)

*Primary Examiner* — Robert R Raevis
(74) *Attorney, Agent, or Firm* — Knobbe, Martens, Olson & Bear LLP

(57) ABSTRACT

A method for collecting and analyzing urine at the time it is released uses a urine collecting tube joined with a canister. Suction is produced in the collecting tube to join the tube with a penis or to the exterior surface of a female urethra orifice. Once suction is achieved the collecting tube stays in place by suction action. When urine flows into the urine collecting tube a sensor triggers a vacuum pump to produce a higher level of suction to flush the urine into the canister where a level sensor determines the quantity of urine received. Various sensors in the canister determine levels of non-urine partials such as occult blood, drugs, salt, and other substances. When urine is no longer detected within the urine tube, the vacuum pump is turned off and a low-level vacuum remains to assure interconnection with the urine tube.

20 Claims, 10 Drawing Sheets

Related U.S. Application Data

(60) Provisional application No. 62/297,096, filed on Feb. 18, 2016.

(51) Int. Cl.
   *G01N 33/487* (2006.01)
   *G01N 33/493* (2006.01)

(58) Field of Classification Search
   USPC ... 73/64.56, 863.01, 863.02, 864.34, 864.51, 73/864.73, 864.81; 600/573, 574, 580, 600/581, 582, 584; 604/329, 349–353
   See application file for complete search history.

(56) References Cited

U.S. PATENT DOCUMENTS

| | | |
|---|---|---|
| 2,571,357 A | 10/1951 | Charles |
| 2,698,016 A | 12/1954 | Andrade et al. |
| 2,739,595 A | 3/1956 | Coles |
| 2,763,266 A | 9/1956 | Evans |
| 2,842,129 A | 7/1958 | Ernstorff |
| 2,867,215 A | 1/1959 | Horton et al. |
| 2,873,740 A | 2/1959 | Wainwright |
| 3,116,734 A | 1/1964 | Terman |
| 3,194,238 A | 7/1965 | Breece, Jr. |
| 3,349,768 A | 10/1967 | Xavier |
| 3,424,163 A | 1/1969 | Gravdahl |
| 3,528,423 A | 9/1970 | Lee |
| 3,601,125 A | 8/1971 | Moss |
| 3,683,914 A | 8/1972 | Crowley |
| 3,742,953 A | 7/1973 | Lee |
| 3,906,952 A | 9/1975 | Zamist |
| 3,918,433 A | 11/1975 | Fuisz |
| 4,023,571 A | 5/1977 | Comerford et al. |
| 4,194,508 A | 3/1980 | Anderson |
| 4,198,979 A | 4/1980 | Cooney et al. |
| 4,200,102 A | 4/1980 | Duhamel et al. |
| 4,246,901 A | 1/1981 | Frosch et al. |
| 4,270,539 A | 6/1981 | Frosch et al. |
| 4,610,675 A | 9/1986 | Truinfol |
| 4,664,663 A | 5/1987 | Brier |
| 4,795,449 A | 1/1989 | Schneider et al. |
| 5,049,144 A | 9/1991 | Payton |
| 5,195,997 A * | 3/1993 | Carns .................. A61F 5/453 600/519 |
| 5,267,969 A | 12/1993 | Hirsch et al. |
| 5,312,379 A | 5/1994 | Rahe |
| 5,346,483 A | 9/1994 | Thaxton, Sr. |
| 5,413,117 A | 5/1995 | Wills |
| 5,424,265 A * | 6/1995 | Weinstein .......... A61M 1/0001 210/282 |
| 5,514,091 A | 5/1996 | Yoon |
| 5,693,001 A | 12/1997 | Salama |
| 5,957,904 A | 9/1999 | Holland |
| 6,120,485 A | 9/2000 | Gustafsson et al. |
| 6,151,721 A | 11/2000 | Whitfield |
| 6,183,454 B1 | 2/2001 | Levine et al. |
| 6,302,303 B1 | 10/2001 | Reynolds |
| 6,394,988 B1 | 5/2002 | Hashimoto |
| D467,338 S | 12/2002 | Rehrig |
| 6,544,242 B1 | 4/2003 | Kido et al. |
| 6,641,567 B1 | 11/2003 | Williams |
| 6,684,414 B1 | 2/2004 | Rehrig |
| 6,699,174 B1 | 3/2004 | Bennett |
| 6,702,793 B1 | 3/2004 | Sweetser |
| 6,740,066 B2 | 5/2004 | Wolff et al. |
| 6,761,710 B2 | 7/2004 | D'acchioli et al. |
| 6,840,925 B2 | 1/2005 | Mishima et al. |
| 6,849,065 B2 | 2/2005 | Schmidt et al. |
| 6,854,427 B2 | 2/2005 | Frink |
| 6,932,797 B2 | 8/2005 | Schmidt et al. |
| 7,018,366 B2 | 3/2006 | Easter |
| 7,465,683 B2 | 12/2008 | McMurray |
| 7,503,911 B2 | 3/2009 | Mishima et al. |
| 7,588,560 B1 | 9/2009 | Dunlop |
| 7,749,205 B2 | 7/2010 | Tazoe et al. |
| 7,875,010 B2 | 1/2011 | Frazier et al. |
| 7,931,634 B2 | 4/2011 | Swiecicki et al. |
| 7,993,311 B2 | 8/2011 | Finger et al. |
| 8,177,760 B2 | 5/2012 | Rome et al. |
| 8,187,238 B1 | 5/2012 | Dupree |
| 8,328,792 B2 | 12/2012 | Nishtala et al. |
| 8,394,074 B2 | 3/2013 | Piette et al. |
| 8,403,901 B2 | 3/2013 | Dunlop |
| 8,454,568 B2 | 6/2013 | Bourke |
| 8,603,056 B1 | 12/2013 | Fallis |
| 8,998,882 B2 | 4/2015 | Knapp et al. |
| 9,028,460 B2 | 5/2015 | Medeiros |
| 9,033,149 B2 | 5/2015 | Terry |
| 2002/0138058 A1 | 9/2002 | Mishima et al. |
| 2003/0004436 A1 | 1/2003 | Schmidt et al. |
| 2003/0010700 A1 | 1/2003 | Schmidt et al. |
| 2003/0185330 A1 | 10/2003 | Hessel et al. |
| 2003/0208112 A1 | 11/2003 | Schmidt et al. |
| 2004/0015141 A1 | 1/2004 | Cheng et al. |
| 2004/0035372 A1 | 2/2004 | Frink |
| 2004/0068780 A1 | 4/2004 | Scott |
| 2004/0079687 A1 | 4/2004 | Muller et al. |
| 2004/0138638 A1 | 7/2004 | Mishima et al. |
| 2004/0143229 A1 | 7/2004 | Easter |
| 2004/0236292 A1 | 11/2004 | Tazoe et al. |
| 2005/0075615 A1 * | 4/2005 | Bonham .................. A61F 5/44 604/327 |
| 2005/0101939 A1 * | 5/2005 | Mitchell ............... A61M 39/10 604/533 |
| 2005/0112975 A1 | 5/2005 | McMurray |
| 2005/0112976 A1 | 5/2005 | McMurray et al. |
| 2005/0137557 A1 | 6/2005 | Swiecicki et al. |
| 2006/0069359 A1 | 3/2006 | Dipalma et al. |
| 2006/0155214 A1 * | 7/2006 | Wightman ............. A61F 5/455 600/574 |
| 2007/0035405 A1 | 2/2007 | Wada et al. |
| 2007/0265589 A1 | 11/2007 | Kitamura |
| 2008/0281282 A1 | 11/2008 | Finger et al. |
| 2008/0287894 A1 | 11/2008 | Van Den et al. |
| 2008/0300448 A1 | 12/2008 | Frazier et al. |
| 2009/0048569 A1 | 2/2009 | Salehi |
| 2009/0078023 A1 | 3/2009 | Mutharasan et al. |
| 2009/0131916 A1 | 5/2009 | Chiu et al. |
| 2009/0270822 A1 | 10/2009 | Medeiros |
| 2009/0306610 A1 | 12/2009 | Van Den et al. |
| 2010/0010459 A1 | 1/2010 | Piette et al. |
| 2010/0234820 A1 | 9/2010 | Tsai et al. |
| 2010/0274156 A1 | 10/2010 | Gorres |
| 2010/0278518 A1 | 11/2010 | Gordon |
| 2011/0028944 A1 | 2/2011 | Chiu et al. |
| 2011/0040271 A1 | 2/2011 | Rogers |
| 2011/0046514 A1 * | 2/2011 | Greenwald ............ A61B 5/208 600/573 |
| 2011/0064586 A1 | 3/2011 | Matsumiya |
| 2011/0178425 A1 | 7/2011 | Nishtala et al. |
| 2011/0251572 A1 | 10/2011 | Nishtala et al. |
| 2011/0265889 A1 | 11/2011 | Tanaka et al. |
| 2015/0320583 A1 * | 11/2015 | Harvie ................... A61F 5/453 604/351 |
| 2016/0310711 A1 * | 10/2016 | Luxon .................. A61M 27/00 |
| 2017/0241978 A1 | 8/2017 | Duval |
| 2017/0280783 A1 | 10/2017 | Nouh |
| 2018/0031461 A1 | 2/2018 | Steckmann et al. |
| 2018/0188231 A1 | 7/2018 | Barakat et al. |

FOREIGN PATENT DOCUMENTS

| | | | |
|---|---|---|---|
| JP | 2001087298 | * | 4/2001 |
| WO | WO 1996/011652 | | 4/1996 |
| WO | WO 1997/001316 | | 1/1997 |
| WO | WO 2004/019836 | | 3/2004 |
| WO | WO 2005/051252 | | 6/2005 |
| WO | 2007/058461 | * | 5/2007 |
| WO | 2008/102808 | * | 8/2008 |

(56) References Cited

FOREIGN PATENT DOCUMENTS

| WO | WO 2009/004291 | 1/2009 |
| WO | WO 2017/142723 | 8/2017 |
| WO | WO 2017/142724 | 8/2017 |

OTHER PUBLICATIONS

International Search Report and Written Opinion issued in PCT Application No. PCT/US2017/016624, dated Apr. 28, 2017, in 11 pages.
International Preliminary Report on Patentability issued in PCT Application No. PCT/US2017/016624, dated Aug. 21, 2018, in 9 pages.
International Preliminary Report on Patentability issued in PCT Application No. PCT/US2017/016626, dated Aug. 21, 2018, in 6 pages.

* cited by examiner

AUTOMATED COLLECTION AND ANALYSIS OF BODY FLUIDS

CROSS-REFERENCE TO RELATED PATENT APPLICATIONS

This application claims priority from prior U.S. provisional patent application Ser. No. 62/297,096 filed Feb. 18, 2016, the entire disclosure of which is incorporated herein by reference.

This application is a continuation-in-part of prior U.S. non-provisional patent application Ser. No. 15/412,049 filed Jan. 22, 2017, the entire disclosure of which is incorporated herein by reference.

BACKGROUND OF THE INVENTION

Field of the Invention

The present invention relates to the collection of body fluids, particularly urine, and to a method of automated collection and analysis Brief Discussion of the Related Art Male urinary collection and analysis is common for medical reasons. This is managed in the prior art with absorbent diapers, indwelling urinary catheters and/or external, non-invasive urine collection devices. Diapers are associated with a high rate of skin breakdown and decubitis ulcer formation while indwelling urinary catheters are a leading cause of urinary tract infections. Accordingly, there has been a great demand for non-invasive external incontinence devices for collecting human urine without exposing the body to continuous urine contact. To avoid leakage, prior art external, non-invasive devices for collecting urine, as exemplified by U.S. Pat. No. 5,263,947 to Kay, U.S. Pat. No. 5,827,247 to Kay and U.S. Pat. No. 5,830,932 to Kay, have incorporated a para-metal seal formed of a ring or annular arrangement of leaves or petals carried by a urine drainage housing and adapted to be adhesively secured to the end of the penis to produce a seal preventing leakage of urine. To enhance the seal, additional sealing layers have been proposed; however, such sealing layers are frequently applied incorrectly when the application requires that the individual applying the device independently establishes an optimal accurate application of the additional sealing layer(s). Application of the additional sealing layer(s) is commonly inaccurate, with the additional sealing layer(s) being applied too proximal or too distal to other sealing layer(s) or with inadequate alignment to achieve an optimal bilaminar seal. Each additional sealing layer must be applied in a specific spatial orientation with respect to previously applied sealing layers, to optimize the leak free duration of each device application. Therefore, there is a need for an external incontinence device which can be applied with a consistent spatial orientation to allow leak-free use especially for females. Furthermore, there is a need for a collection device with analytic capabilities.

BRIEF DISCUSSION OF RELATED ANALYTICS

These devices are known in applications for sensing protein, screening for diseases, detection of Nanocantilevers point mutations, blood glucose monitoring, detection of chemical and biological warfare agents, and have been used in nanoelectromechanical systems. Molecules adsorbed on a microcantilever cause vibrational frequency changes and deflection. Viscosity, density, and flow rate can be measured by detecting these physical changes. This development has increased the sensitivity limit to the extent that researchers can now visualize the counting of molecules. With the ability of high throughput analysis of analytes and ultra-sensitive detection, this technology holds promise for the next generation of miniaturized and highly sensitive sensors. Molecular diagnostic devices are getting smaller with the advancement of miniaturization techniques. There is increasing interest in the field of bio sensor research on miniaturized platforms. Miniaturization is essential for in-vivo physiological monitoring, multiple specificity sensor arrays, sensor portability and minimized sample volumes. Conventional biosensors need extensive packaging, complex electronic interfacing and regular maintenance. These new micro-sensors have advantages over conventional analytical techniques in terms of high sensitivity, low cost, simple procedure, low analyte requirement, non-hazardous procedures and quick response.

Sodium Chloride:

A poly-silicon nanowire is used to sense and measure sodium chloride concentration in solution. The Department of Communications Engineering, at Yuan Ze University, Taiwan, has developed a NaCl concentration; ion sensitive field-effect transistor; using poly-silicon nanowires. This sensor was fabricated by top-down technique for sodium chloride concentration measurement. The results showed that the smallest threshold voltage and the best resolution were 1.65 V and 0.41 µM, respectively. This sensor is able to be reused more than 50 times while maintaining acceptable performance and showed good linearity of calibration within a wide range of concentrations. Based on these results, the proposed sensor has potential to be used for measuring complicated samples with suitable modification on the surface of nanowires.

Moisture:

In yet another development, Professor Alan Lakso of Cornell University has engineered a micro-chip which is able to hold water in a small cavity and exchange moisture from that cavity with moisture in its environment via a nano-porous membrane. The chip measures any changes in the pressure within the cavity that result from water entering or being drawn out. In order to relay the data it gathers, the chip may be wired to a Wi-Fi card, a data logger, or other device for gathering and transmitting information. The chip can last outdoors for at least a few years, although freezing temperatures may cause failure.

Liquid Level:

For liquid level sensing, optical infrared devices are commercially available and can be used to replace mechanical type float switches while providing high precision level control. These devices have compact construction with no moving parts so as to provide high reliability. They meet or exceed all common safety standard and are RoHS compliant. Alternately, ITV plc of the UK produces a water level sensor part number 6336 commonly used for this intended purpose.

Occult Blood:

For occult blood detection, optical sensors are available, as for example from Sonotec Products, EU. to detect the smallest amounts of blood in dialysates on transparent tubes non-invasively. As the wavelength is adapted to the transmittance of blood, the international standard IEC 60601-2-16:2008 for medical electrical devices is fulfilled reliably. Hence, these sensors are able to detect as small as 0.04% of blood in an isotonic saline solution. For instance, one such commercially available detector meets high safety standards and features a serial interface. With simple commands, this sensor can be tested and sensitivity level adjusted. Such a device is suitable for all tasks that require the optical detection of transmission differences of liquids in transparent tubes. Due to the high sensitivity of these sensors it is even possible to detect when a tube filled with a clear fluid runs empty.

Drugs:

The Amedicheck Panel Urine Drug Testing Cup is available through TransMed Co. LLC, Cumming, Ga. This device is used to determine the presence of the following substances: Marijuana (THC), Opiates (OPI), Methamphetamines (METH), Cocaine (COC), Phencyclidine (PCP), Amphetamines (AMP), Oxycodone (OXY), Barbiturates (BAR), Benzodiazepine (BZO), Methadone (MTD), Tricyclic Antidepressants (TCA), and Ecstasy (MDMA).

Proteins:

Recently, numerous biosensors for detecting specific biomolecules such as DNA, proteins and antibody-antigen have been studied for a clinical and industrial demand with the progress of life science. There has been considerable attention directed to protein molecules since the occurrence of disease is well known at this level. Even though several techniques for the detection of proteins such as optical, mass spectrometry, and electrochemical measurement are in existence, field effect transistor based biosensors, which are fabricated by semiconductor integrated circuit techniques, have lately attracted attention because of its various advantages in miniaturization, standardization, mass-production and especially suitable configuration for an on-chip integration of both the sensor and measurement system. A gate field effect transistor biosensor for the detection of streptavidin-biotin protein complexes in a silicon micro-fluidic channel has been developed. The connection between this device and a micro-fluidic system could be achieved offering merits of isolation between the device and solution, compatibility with integrated circuit technology and applicability to the micro total analysis system. Such a device was fabricated combining semiconductor integrated circuit and micro-electro-mechanical system techniques.

SUMMARY OF THE INVENTION

The presently described apparatus includes a urine tube and a canister. The urine tube is adapted for joining with the human urethra, either male or female, and as such, enables reception of urine discharges. Suction of about 5 inches Hg is produced within the apparatus. This suction enables the temporary joining between the interface portion and the urethra. The apparatus is worn at times when urination is expected or desired and may be disconnected and removed from, and reconnected to an individual at will. The urine tube is adapted by size for receiving an individual's penis or with a flared end to engage a female urethra where in both cases suction is used for engagement. Once sealed, the suction source may be released while leaving a light vacuum within the urine tube thereby maintaining the seal. In both the male and female approach, suction within the tube may be released at any time by releasing suction. However, suction is present during urination which will send urine into the urine canister. A liquid sensor signals when urine is present. This produces a higher suction level within the urine tube, drawing the urine into the canister. When the liquid sensor no longer senses the presence of liquid, the vacuum generator closes-down while leaving a low-level suction for maintaining connection of the urine tube to the urethra. Sensors within the canister are able to detect substances within the urine. For instance, using known sensors and analytic techniques: Quantitative analysis of occult blood, proteins, glucose, drugs, and various chemical compositions can be determined. This information is delivered to a digital processor for data logging and analysis including plotting values against time. Comparison of measured values relative to standards, enables prediction of medical conditions including illness. Therefore, it is an object of the invention to maintain a tube at a urethra outlet. It is another object to provide a means for allowing urination to occur without interrupting a person's sleep or activities. It is a further object to continuously monitor a patient's biological signs through urine sampling and analysis. It is a still further object to collect urine in a system that is low cost, easily operated, and portable to be useful by paramedics in the field. These and other aspects of embodiments herein described will be better appreciated when considered in conjunction with the following description and the accompanying drawings. It should be understood, however, that the following descriptions, while indicating preferred embodiments and numerous specific details thereof, are given by way of illustration and not of limitation. Changes and modifications may be made within the scope of the embodiments herein presented without departing from the spirit thereof. Unless otherwise indicated expressions of singularity shall include plurality and vice-versa, while expressions of the alternative shall be considered nonexclusive.

BRIEF DESCRIPTION OF THE DRAWINGS

Illustrations in the drawing sheets presented herein are examples only and should not be taken as limiting. The same reference numeral refers to the same element as it may appear in multiple figures and drawing sheets.

DETAILED DESCRIPTION

Figure 5:
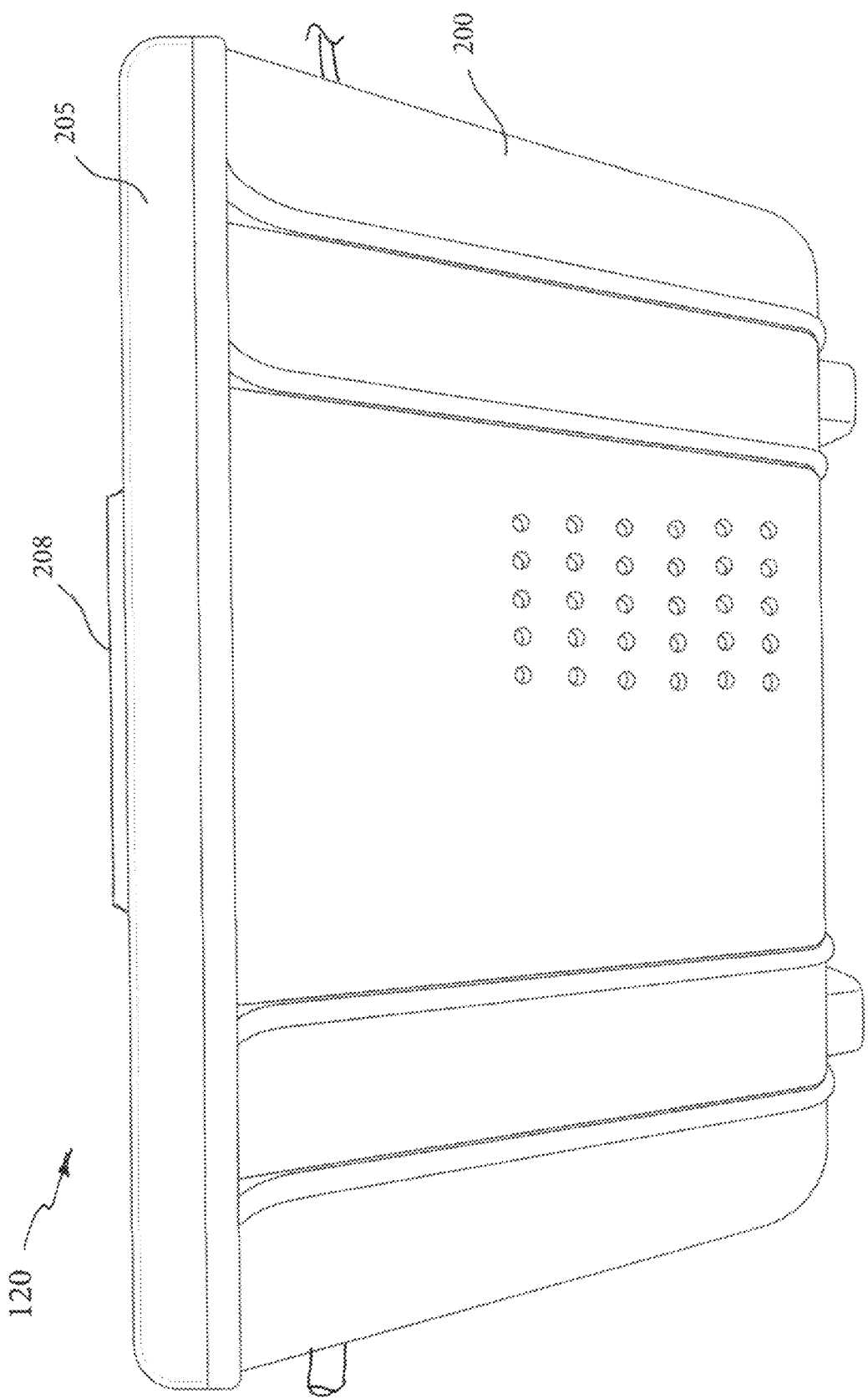
FIG. 5 is a side elevation view of an enclosure of the apparatus.
Figure 6:
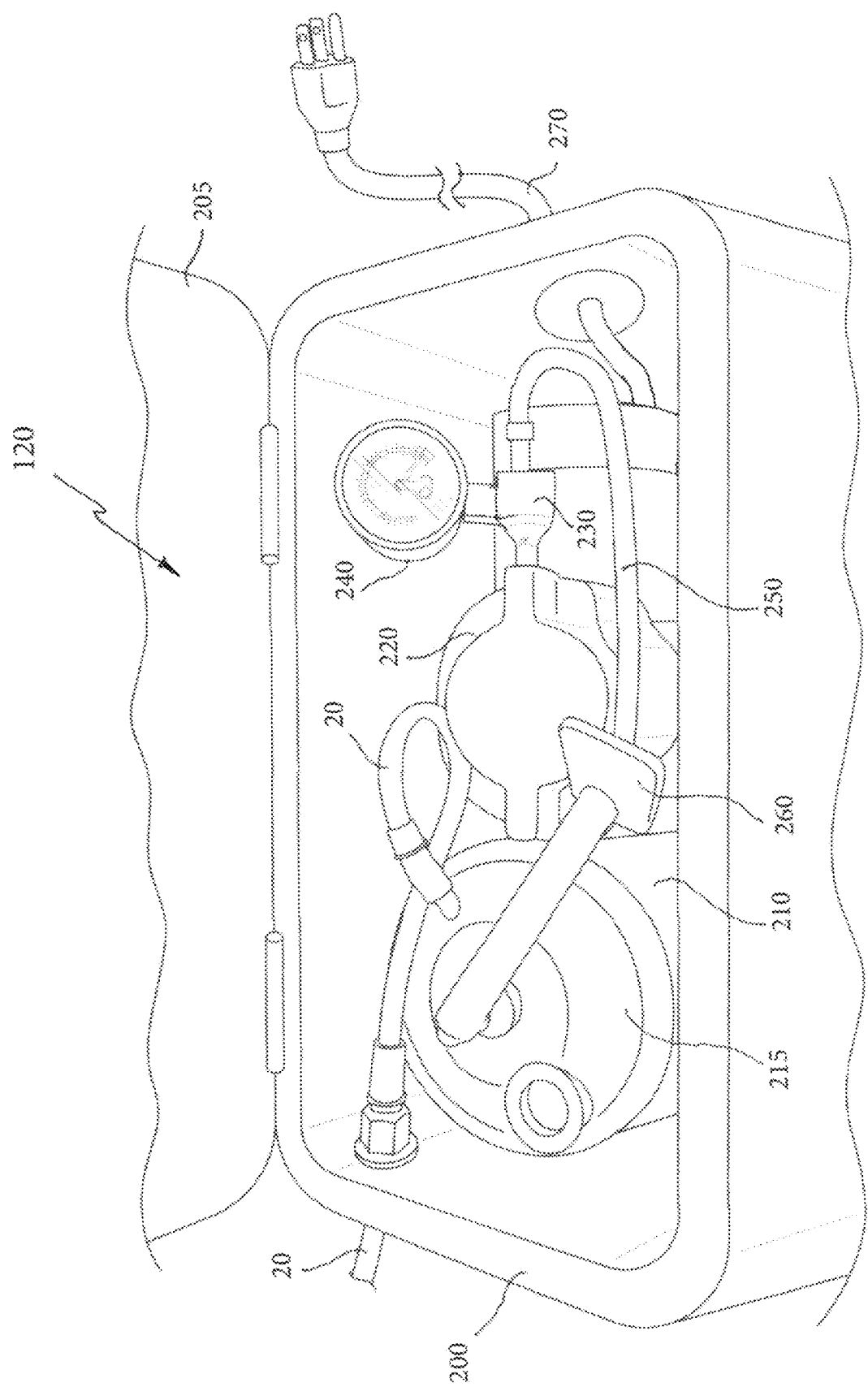
FIG. 6 is a perspective view of an open top thereof showing components of a receiver portion of the apparatus.

As shown in the attached drawing figures, a collector-analyzer apparatus includes an interface portion 110 (FIGS. 1 and 2) and a receiver portion 120 (FIGS. 5 and 6). These two portions are joined by a flexible interconnection tube 20 so that they may be conveniently set some distance apart during operation.

Figure 1:
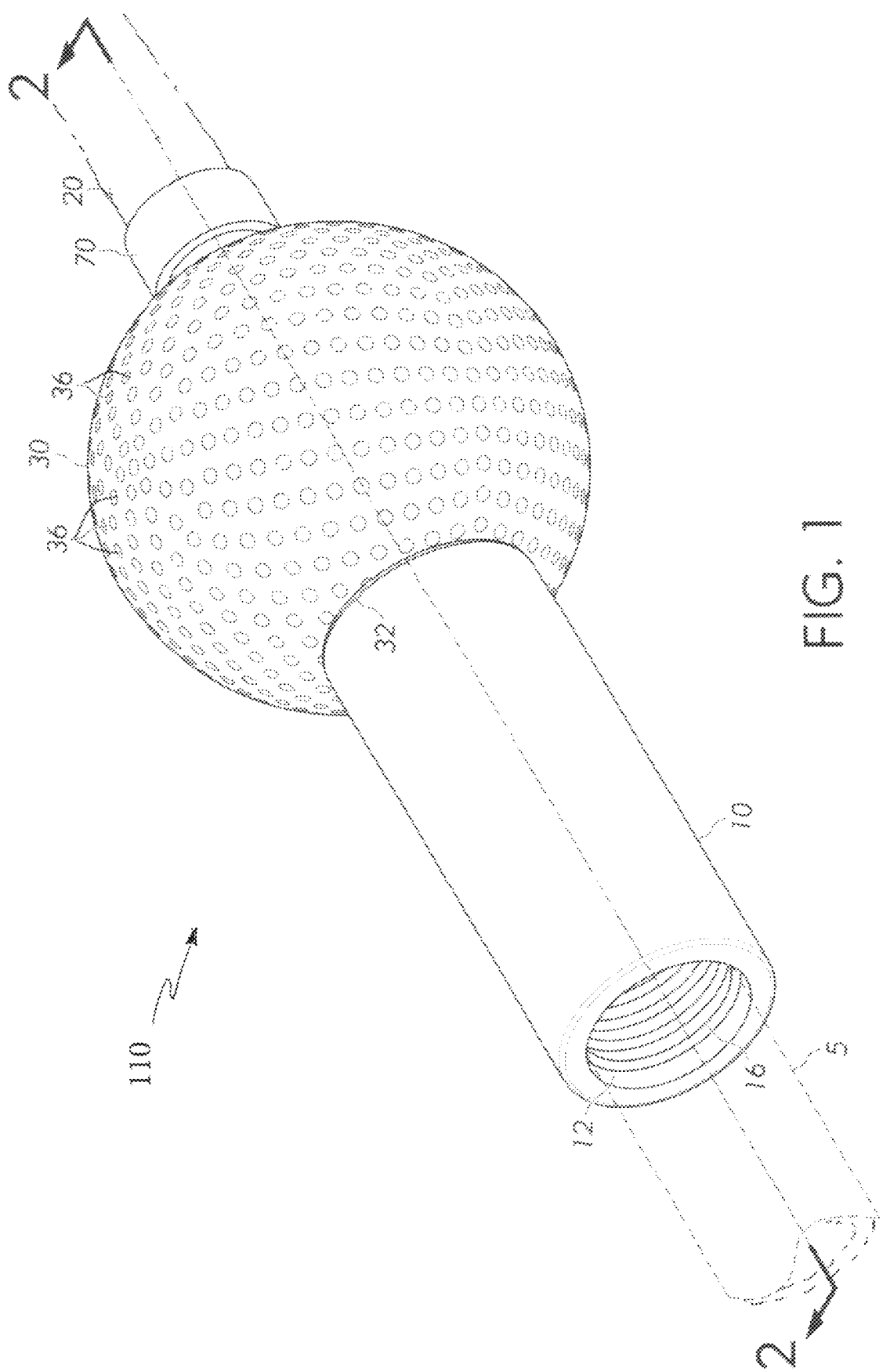
FIG. 1 is a proximal perspective view of an interface portion of a described apparatus showing a urine tube extending proximally from an enclosure.
Figure 2:
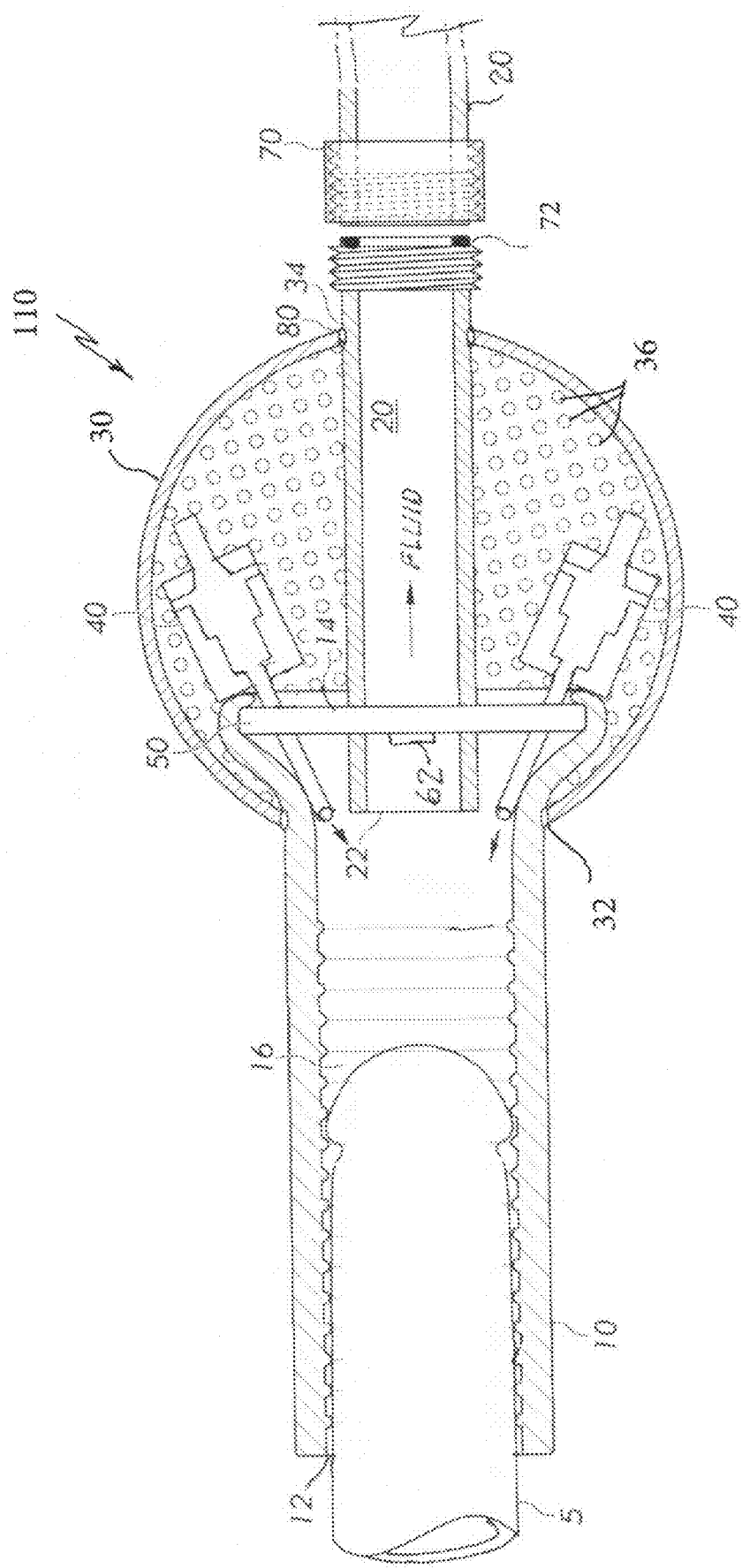
FIG. 2 is a section view thereof taken along cutting plane line 2-2 in FIG. 1 and showing a penis interface with a urine tube.

As shown in FIGS. 1 and 2 interface portion 110 is adapted for joining with the urethra, either male or female, and as such, enables reception of discharged urine; see the arrow labeled "fluid" in FIG. 2. These figures illustrate penis 5 which is inserted into proximal open end 12 of urine tube 10. Tube 10 may be of a transparent soft elastomeric material such as a silicone gel. Internal ribs 16 within tube 10 are shown and it is pointed out that they provide an improved gripping of tube 10 around penis 5 so that penis 5 is secured within tube 10 by suction action with no leakage. Shown also, are a spherical enclosure 30, vent holes 36 to allow air to enter enclosure 30, and proximal entry 32 in enclosure 30 holds tube 10 securely in place.

FIG. 2 illustrates further the character of interface portion 110 including rigid disc 50 shown edgewise, which may be a circular flat object secured within distal end 14 of urine tube 10. It is pointed out that urine tube 10, being of an elastomeric material, may be stretched around the periphery of disc 50 to hold it in place axially relative to urine tube 10. Disc 50 has a central hole 14 which accepts proximal end 22 of interconnection tube 20 securing it in place with a tight fit. Fluid sensor 62 may be mounted on disc 50 as shown and as will be described may be functional in the process of generating suction when urine is present within urine tube 10. It is suction that draws urine from tube 10 to tube 20. One or more electromechanical vent valves 40 are contained within enclosure 30 and mounted through holes in disc 50 which secures valves 40 in place. Valves 40, when open, provide air flow into urine tube 10 but prevents fluid from passing outward (one-way valve). Valves 40 are of such size as to allow some air to enter tube 10, and while suction overcomes the tendency of pressure rising due to this air inflow, to maintain a negative pressure within tube 10 suction is increased to compensate. Fluid sensor 62 may also have a companion sensor to monitor air pressure (suction). Connector 70 is used to allow separation of interconnection tube 20 to allow a more comfortable management of the joining of urine tube 10 with the penis 5 or the urethra and to allow a user to move about freely when the apparatus is not being used. Electrical wires (see FIG. 9) will also be disconnected at that time. An o-ring 72 is used to seal connector 70.

Figure 3:
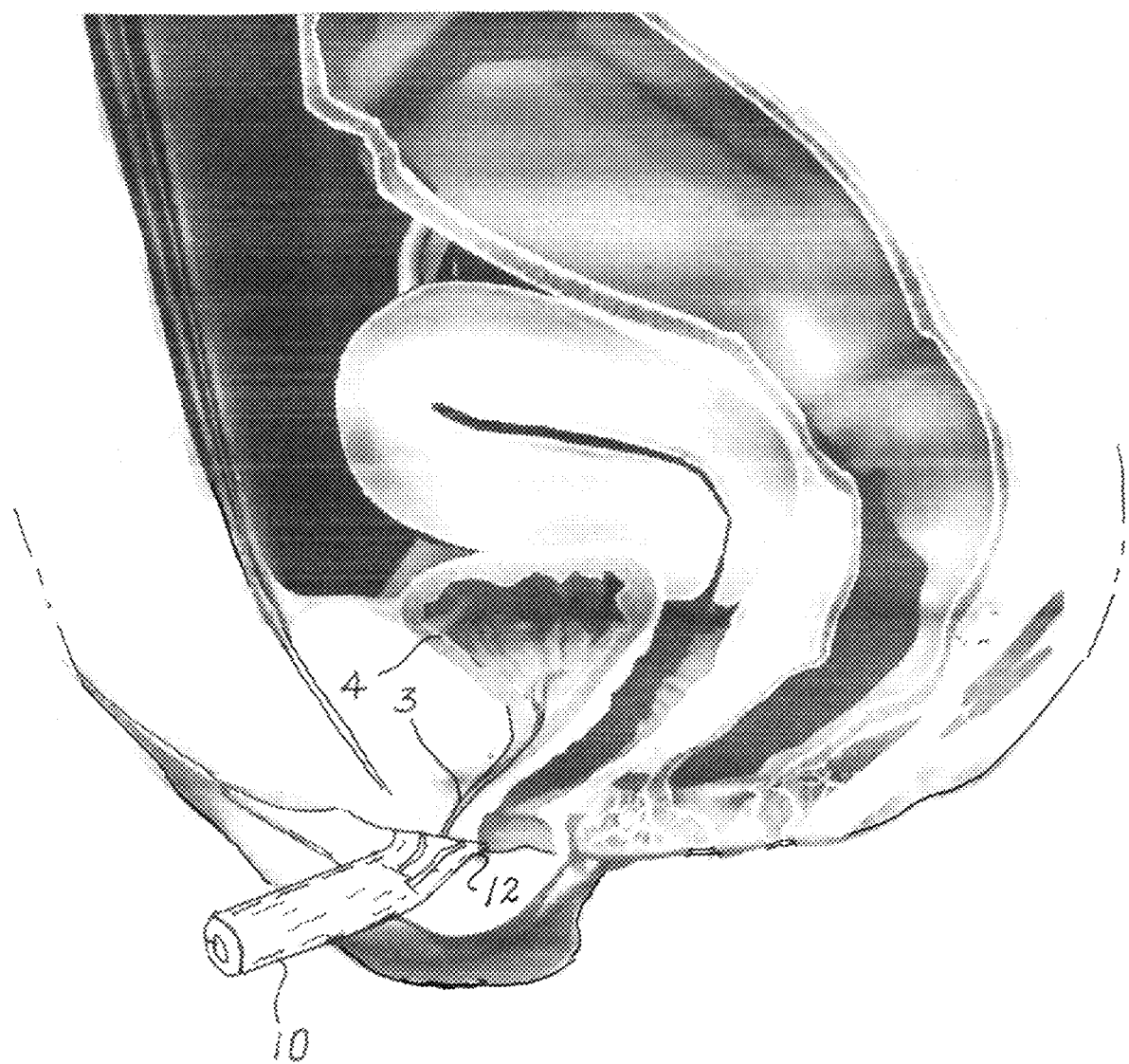
FIG. 3 is a vertical section view of a typical female abdomen with a peritoneum area showing a urethral interface with a urine tube of the apparatus.

FIG. 3 illustrates the joining of urine tube 10 with the female urethra 3 at the urethral orifice which is adjacent to the tissue surface of the vestibule. As shown, urine tube 10 may be flared or forced into a flared condition thereby conforming opening 12 as a suction-cup type joint for improved suction holding.

Figure 4:
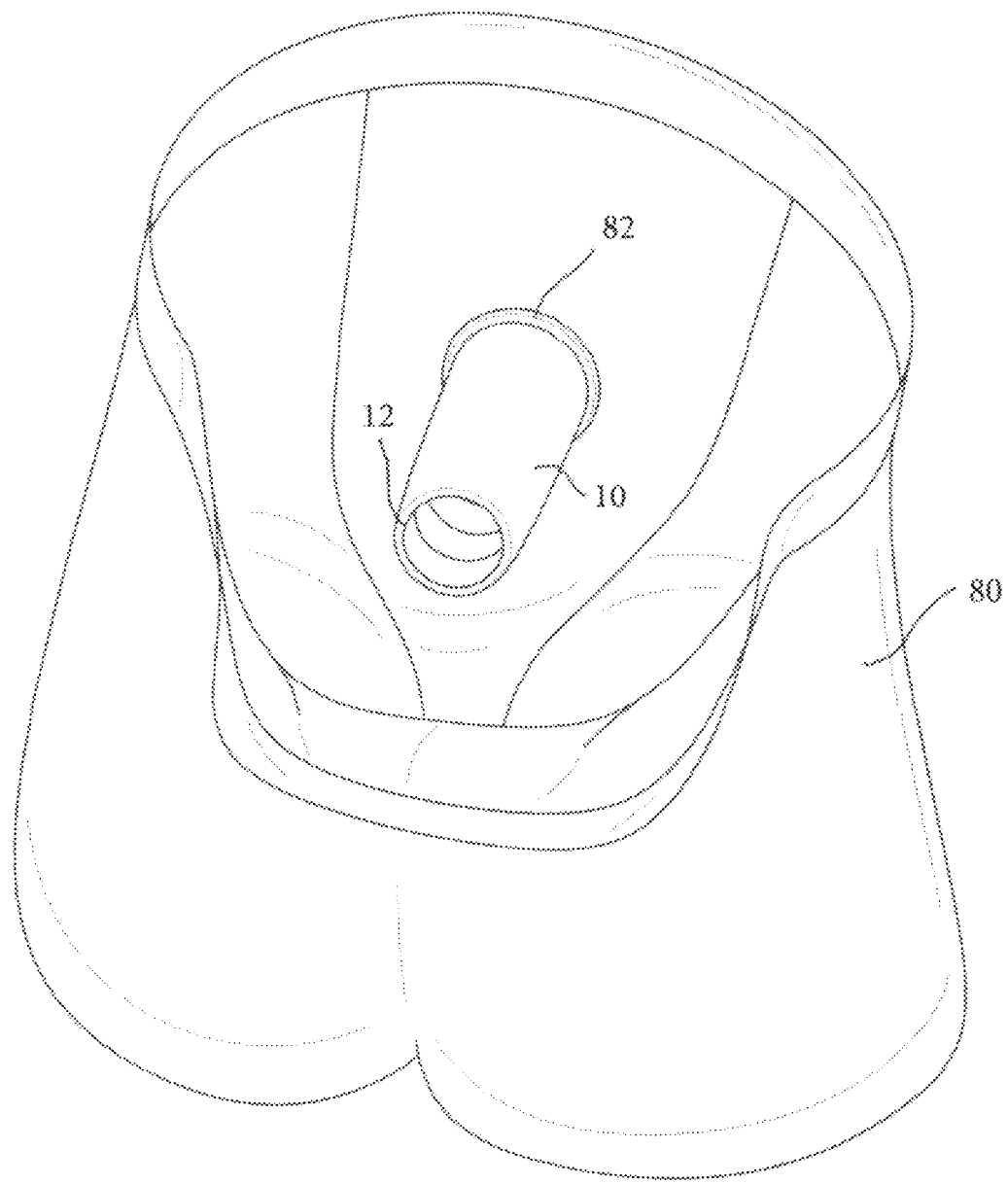
FIG. 4 is a perspective view of a garment interface with the urine tube.

FIG. 4 shows an enablement wherein urine tube 10 is engaged with an undergarment 80 such as an underwear, under-pant, panty, diaper or similar item worn by an individual when using the apparatus. As shown, urine tube 10 may be inserted through an opening or a slit, fold, etc. 82 in undergarment 80, wherein opening 82 may have a strong elastic edge or closure capable of helping to hold urine tube 10 in place so that axial movement between urine tube 10 and undergarment 80 is minimized and loss of suction attachment is also minimized. In this case urine tube 10 is secured in place by both garment 80 as well as by suction as previously described.

In FIG. 5 case 200 may include a hinged cover 205 as shown. Cover 205 may have a digital processor system 208 mounted within. System 208 may be a Seetec model W759 digital processor with seven-inch LCD monitor resistive touch panel and WIFI, Bluetooth, and GPS communication capability or any equivalent as will be known to those of skill in the art.

In FIG. 6, as shown, case 200 may enclose graduated canister 210 with its attached, sealed lid 215. Case 200 may also house motor driven vacuum pump 220 with its attached shut-off valve 230 and vacuum gauge 240. Suction tube 250, may interconnect shut-off valve 230 with canister lid 215 and may include filter 260 which may be used to prevent vacuum pump oil from traveling upstream into canister 210 and also may prevent bacteria from traveling downstream to reach pump 220 where it would be exhausted to the environment. Vacuum pump 220 may be powered by AC current via power cord 270 as shown, or alternately may be powered by a DC battery pack with inverter (not shown). Suction (low pressure) in canister 210 is developed in interconnection tube 20 and urine tube 10 for application at penis 5 or urethra 3 as previously described. Urine, when present, is therefore sucked through urine tube 10, interconnection tube 20, and into canister 210 where it can be analyzed. In like manner, other fluids may be suctioned into canister 210 for analysis.

Figure 7:
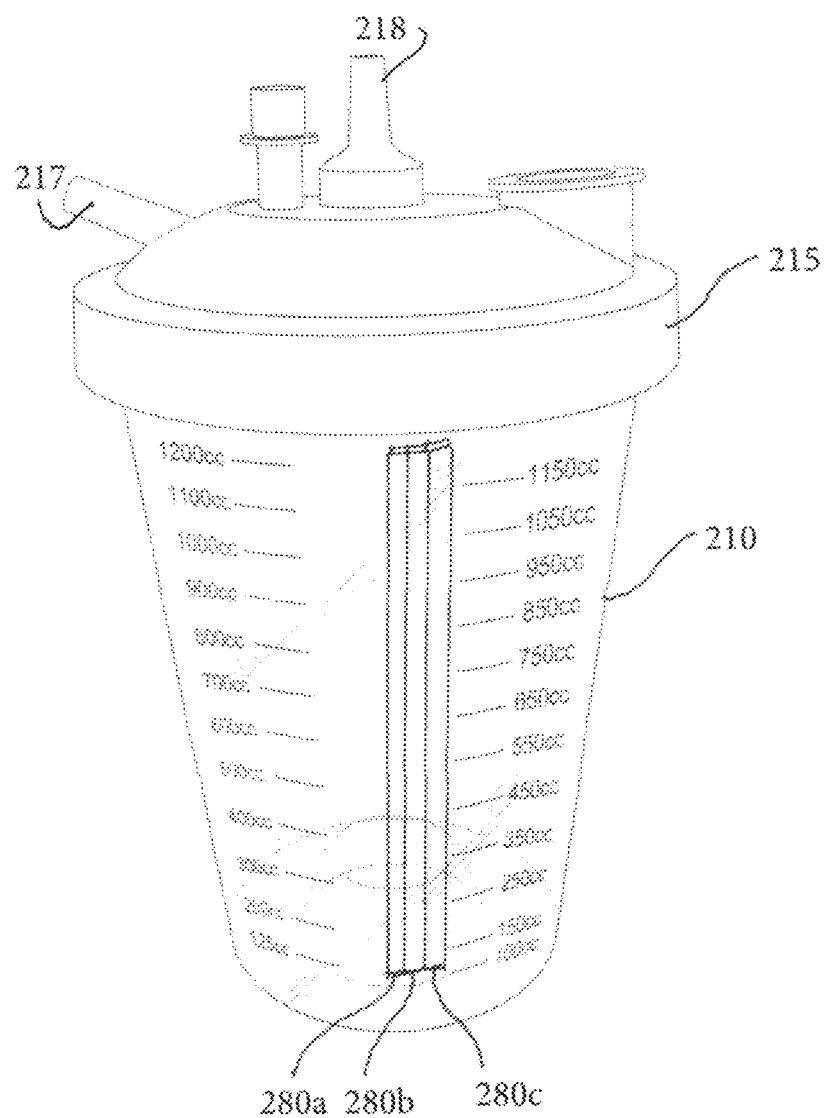
FIG. 7 is a side view of a canister of the apparatus.

FIG. 7 illustrates graduated canister 210 with lid 215. As described, urine is delivered into canister 210 via interconnection tube 20 which is fitted to inlet 217 of lid 215. Suction is applied at fitting 218 of lid 215. Sensors 280a, 280b, and 280c are representative of a wide variety of sensor and sensory materials that may be utilized in characterizing collected samples of urine or other fluids. Such sensors may be mounted, as shown, in strips on the interior side surface of canister 210 as shown or may have another form and may be mounted in other ways. Such sensors may be used to detect liquid level, trace chemicals, biological agents, occult blood, and other foreign agents or components of collected urine as described in the foregoing Brief Discussion of Related Analytics.

Figure 8:
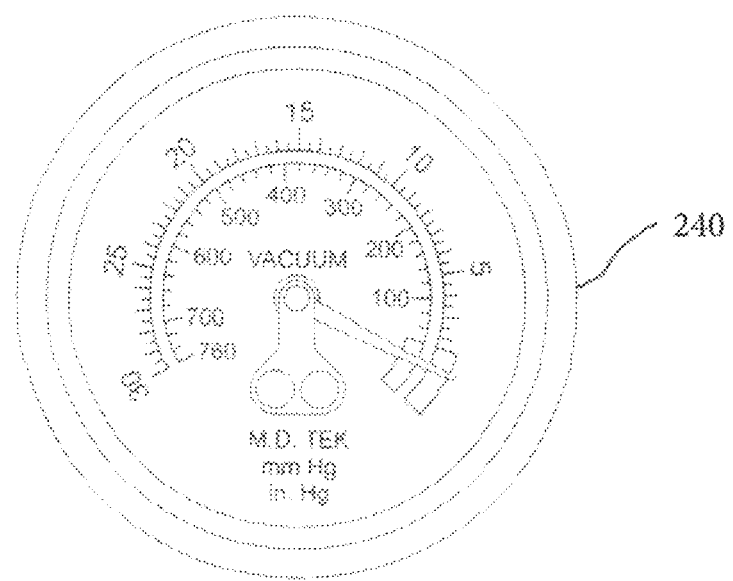
FIG. 8 is a front view of a vacuum gauge of the apparatus.
Figure 10:
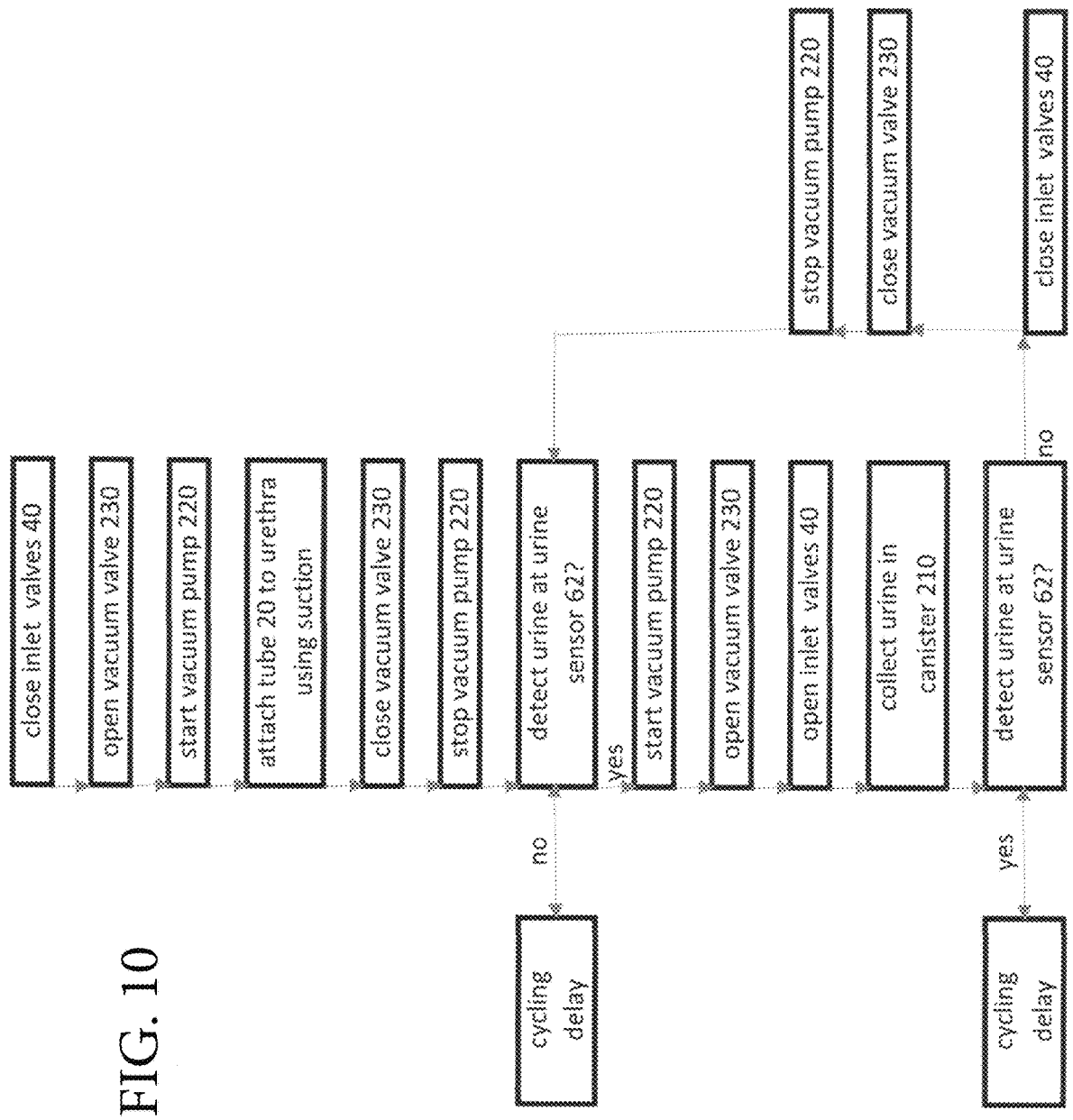
FIG. 10 is a logic flow diagram illustrating the described method.

FIG. 8 illustrates vacuum gauge 240 capable of reading vacuum in mm Hg on the inner scale and inches of Hg on the outer scale with higher vacuum (stronger suction/lower pressure) increasing in a counter-clockwise movement of the gauge's indicator. Suction of about 5 inches (145 mm) Hg is controlled as a maximum set point by gauge 240 so that valve 230 is automatically closed when vacuum level attempts to exceed this value thereby preventing damage to the penis sheath or to the tissues of the labia minora/vestibule. Vacuum operations include two modes: Standby and Active. In Standby mode, a low level of suction is created after which vacuum pump 220 is shut down. This low level of suction maintains attachment of the proximal end 12 of urine tube 10 to penis or urethral aperture. During standby mode valves 40 and 240 are held closed to preserve suction for the maintenance of attachment of urine tube 10. Standby mode may be held throughout the night, but if urine enters tube 10 while the system is in Standby mode, urine sensor 62 immediately triggers Active mode operation through computer 208. Sensor 62 signals computer 208 which causes pump 220 to turn on and valves 40 and 240 to open. Suction is generated at urine tube 10 which overcomes air inflow through valves 40 to maintain suction which forces urine through tubes 10 and 20 and into canister 210. When sensor 62 no longer detects the presence of urine, the reverse occurs so that the apparatus resumes the Standby mode. In an alternate mode of operation, vacuum pump 220 may be on during standby to assure that enough suction is produced to hold attachment of urine tube 10 as described above. FIG. 10 shows the above operation in detail.

Figure 9:
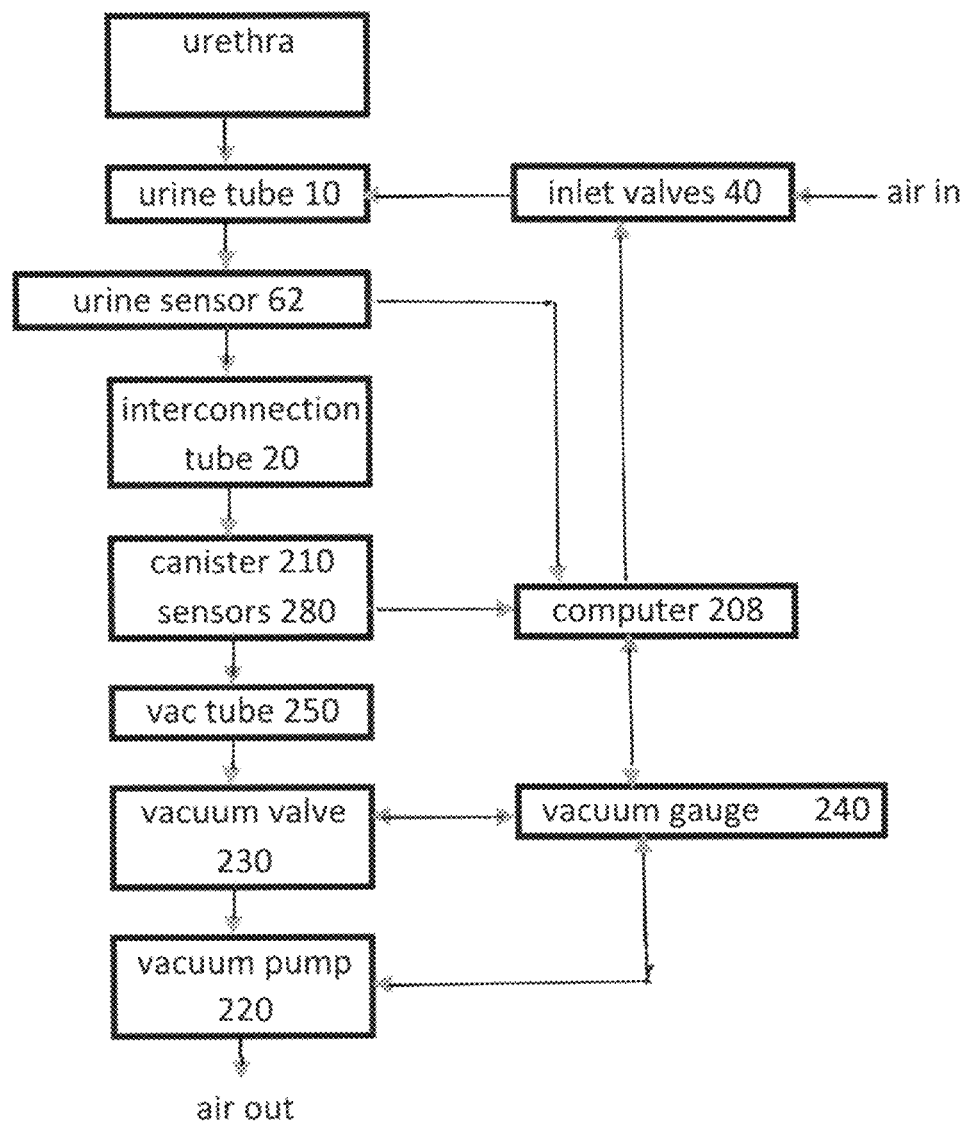
FIG. 9 is a schematic diagram of the apparatus defining interconnections.

FIG. 9 shows how several interconnections between components of the described system are joined. Computer 208 controls operations. Urine tube 10 is joined to the urethra by suction during Standby mode. When urine enters urine tube 10 urine-sensor 62 detects it and signals computer 208 which, in turn, signals vacuum gage 240 and opens vacuum valve 230 and also turns on vacuum pump 220. Computer 208 signals inlet valves 40 thereby opening them. With vacuum pump 220 now operating and with vacuum valve 230 open, suction is applied through vacuum tube 250 and canister 210 and interconnection tube 20 and urine tube 10 which flushes the urine into canister 210. When urine sensor 62 no longer senses urine in urine tube 10 the signal to computer 208 is extinguished and signals are sent to inlet valves 40 and, through vacuum gauge 240 to close vacuum valve 230 and close-down vacuum pump 220. In the alternative, standby mode may be entered with vacuum valve 230 and/or vacuum pump 220 throttled to achieve a low suction level as monitored by vacuum gauge 230. When urine is present in canister 210 sensors 280 determine the presence of, and quantitative characteristic of several species within the urine such as: proteins, drugs, occult Blood, sodium chloride (NaCl), and other elements, compounds, and substances. Such content may be determined down to micro levels using one or more of the techniques described in the foregoing Brief Discussion of Related Analytics. It is within the skill level of those experienced in the computer arts to define an algorithm or software program such as defined in FIG. 10 to carry out the processes described in FIG. 9. It is within the skill level of those experienced in systems engineering to define a means for interconnecting the components of the apparatus as shown in FIG. 9.

It should be recognized that the described apparatus may be adapted for use with animals other than humans. For instance, there is a need for taking and analyzing urine samples of farm animals such horses, mules, cows, and non-farm animals and other mammals.

In this description, embodiments are described as a plurality of individual parts, and methods as a plurality of individual steps and this is solely for the sake of illustration. Accordingly, it is contemplated that some additional parts or steps may be added, some parts or steps may be changed or omitted, and the order of the parts or steps may be re-arranged, while maintaining the sense and understanding of the apparatus and methods as claimed.

What is claimed is:

1. A method of collecting and analyzing body fluids using a collector-analyzer apparatus, the method comprising:
    enabling a proximal end of a flexible urine tube having internal ribs for engaging and holding a penis therein;
    stretching a distal end of said urine tube around a rigid disc within a vented enclosure;
    joining an air vent valve with said rigid disk for injecting air from said vented enclosure into said proximal end of said urine tube;
    securing a proximal end of an interconnection tube by said rigid disk and into said distal end of said urine tube;
    connecting a distal end of said interconnection tube with a canister for collecting said body fluids;
    producing suction within said canister, said interconnection tube and said urine tube;
    admitting air into said urine tube through said air vent valve to a controlled set point of suction;
    sensing a presence of said body fluids in said urine tube by a fluid sensor engaged with said rigid disk; and
    conducting said body fluids from said urine tube through said interconnection tube and into said canister.

2. The method of claim 1, wherein conducting said body fluids from said urine tube into said canister comprises:
    opening a vacuum valve;
    turning on a vacuum pump; and
    flushing said body fluids into said canister.

3. The method of claim 2, further comprising:
    analyzing the body fluids within said canister to determine the presence of substances in said body fluids.

4. The method of claim 3, wherein said substances include one or more of minerals, pathogens, drugs, compounds, or occult blood.

5. The method of claim 3, further comprising determining a quantitative characteristic of at least one substance in said body fluids.

6. The method of claim 1, further comprising:
    sensing when body fluids are no longer present in said urine tube said method further comprises:
    closing said vacuum valve; and
    closing down said vacuum pump.

7. The method of claim 1, further comprising:
    joining a penis with a proximal end of said urine tube;
    sensing a vacuum level in said urine tube; and
    admitting air into said urine tube to adjust said vacuum level therein.

8. The method of claim 1, further comprising analyzing said body fluids in the canister using one or more sensors to determine a characteristic of a substance in said body fluids.

9. The method of claim 8, further comprising signaling said computer with results of said analyzing.

10. A method of collecting and analyzing body fluids, the method comprising:
    closing an air inlet valve and opening a vacuum valve;
    starting a vacuum pump;
    attaching a urine tube to one of a penis and a urethra by suction;
    closing said vacuum valve;
    stopping said vacuum pump;
    detecting body fluids within said urine tube;
    opening said vacuum valve;
    starting said vacuum pump;
    opening said air inlet valve;
    collecting said body fluids;
    closing said air inlet valve;
    closing said vacuum valve; and
    stopping said vacuum pump.

11. A method of collecting and analyzing body fluids using a collector- analyzer apparatus, the method comprising:
    stretching a distal end of a urine tube for engaging a female urethra around a rigid disc within a vented enclosure;
    joining an air vent valve with said rigid disk for injecting air from said vented enclosure into said proximal end of said urine tube;
    securing a proximal end of an interconnection tube by said rigid disk and into said distal end of said urine tube;
    connecting a distal end of said interconnection tube with a canister for collecting said body fluids;
    producing suction within said canister, said interconnection tube and said urine tube;
    admitting air into said urine tube through said air vent valve to a controlled set point of suction;
    sensing a presence of said body fluids in said urine tube by a fluid sensor engaged with said rigid disk; and
    conducting said body fluids from said urine tube through said interconnection tube and into said canister.

12. The method of claim 11, wherein conducting said body fluids from said urine tube into said canister comprises:
    opening a vacuum valve;
    turning on a vacuum pump; and
    flushing said body fluids into said canister.

13. The method of claim 12, further comprising analyzing the body fluids within said canister to determine the presence of at least one substance in said body fluids.

14. The method of claim 11, further comprising:
joining a female urethra with a proximal end of said urine tube;
sensing a vacuum level in said urine tube; and
admitting air into said urine tube to adjust said vacuum level therein.

15. The method of claim 11, wherein said urine tube is flared for improved suction holding.

16. A method of collecting and analyzing body fluids, the method comprising:
closing an air inlet valve and opening a vacuum valve;
starting a vacuum pump;
attaching a urine tube to a female urethra by suction;
closing said vacuum valve;
stopping said vacuum pump;
detecting body fluids within said urine tube;
opening said vacuum valve;
starting said vacuum pump;
opening said air inlet valve;
collecting said body fluids;
closing said air inlet valve;
closing said vacuum valve; and
stopping said vacuum pump.

17. The method of claim 16, further comprising analyzing the collected body fluids to determine the presence of at least one substance in said body fluids.

18. The method of claim 17, wherein said at least one substance includes one or more of minerals, pathogens, drugs, compounds, or occult blood.

19. The method of claim 16, wherein said urine tube is flared for improved suction holding of the urethra.

20. The method of claim 16, further comprising determining a quantitative characteristic of a substance in said body fluids.

* * * * *

UNITED STATES PATENT AND TRADEMARK OFFICE
CERTIFICATE OF CORRECTION

PATENT NO. : 10,682,124 B2
APPLICATION NO. : 15/416272
DATED : June 16, 2020
INVENTOR(S) : Landon Duval Page 1 of 1

It is certified that error appears in the above-identified patent and that said Letters Patent is hereby corrected as shown below:

In the Specification

In Column 1, Line 21, delete "analysis" and insert --analysis.--.

In Column 1, Line 27, delete "decubitis" and insert --decubitus--.

In Column 2, Line 8, delete "bio sensor" and insert --biosensor--.

In the Claims

In Column 7, Line 47, Claim 1, delete "disk" and insert --disc--.

In Column 7, Line 51, Claim 1, delete "disk" and insert --disc--.

In Column 7, Line 60, Claim 1, delete "disk" and insert --disc--.

In Column 8, Line 42, Claim 11, delete "collector- analyzer" and insert --collector-analyzer--.

In Column 8, Line 47, Claim 11, delete "disk" and insert --disc--.

In Column 8, Line 51, Claim 11, delete "disk" and insert --disc--.

In Column 8, Line 60, Claim 11, delete "disk" and insert --disc--.

Signed and Sealed this
Twenty-seventh Day of August, 2024

Katherine Kelly Vidal
*Director of the United States Patent and Trademark Office*